United States Patent [19]

Bentall

[11] Patent Number: 4,471,787
[45] Date of Patent: Sep. 18, 1984

[54] DEVICE FOR APPLYING A HIGH FREQUENCY ELECTROMAGNETIC FIELD TO LIVING TISSUE TO PROMOTE HEALING THEREOF

[76] Inventor: Richard H. C. Bentall, The Basement, 7 Penzance Pl., London W11 4PE, Great Britain

[21] Appl. No.: 422,558

[22] Filed: Sep. 24, 1982

Related U.S. Application Data

[60] Continuation-in-part of Ser. No. 205,749, Nov. 10, 1980, Pat. No. 4,429,698, which is a division of Ser. No. 74,926, Sep. 13, 1979, abandoned.

[30] Foreign Application Priority Data

Sep. 24, 1981 [GB] United Kingdom ............... 8128909
Sep. 24, 1981 [GB] United Kingdom ............... 8128910

[51] Int. Cl.³ ............................................. A61N 1/40
[52] U.S. Cl. ..................................................... 128/804
[58] Field of Search ............................. 128/422, 804

[56] References Cited

U.S. PATENT DOCUMENTS

| 2,220,269 | 11/1940 | Patzold | 128/804 |
| 2,249,936 | 7/1941 | Birtcher | 128/804 |
| 2,656,839 | 10/1953 | Howard | 128/422 |
| 3,077,195 | 2/1963 | Folsche | 128/804 |

FOREIGN PATENT DOCUMENTS

| 1247504 | 8/1967 | Fed. Rep. of Germany | 128/804 |
| 48005 | 5/1980 | Intern. Pat. Institute | 128/804 |
| 2027594 | 2/1980 | United Kingdom | 128/804 |

Primary Examiner—William E. Kamm
Attorney, Agent, or Firm—Steele, Gould & Fried

[57] ABSTRACT

A portable therapy device for attachment to a patient to promote tissue healing by exposure to an r.f. field, comprises an oscillator (5) which energizes an antenna having a transmitting element (1) the natural directive pattern of which is modified by a reflector (8) and a parasitic element (10) such that a major part of the r.f. field emitted by the antenna passes to the patient. In another embodiment the antenna is configured to produce a spatially substantially uniform field strength over the area of the patient being treated. The device subjects the tissue to r.f. power levels which produce no significant tissue heating.

14 Claims, 4 Drawing Figures

DEVICE FOR APPLYING A HIGH FREQUENCY ELECTROMAGNETIC FIELD TO LIVING TISSUE TO PROMOTE HEALING THEREOF

This application is a continuation-in-part application of copending application Ser. No. 205,749, filed Nov. 10, 1980, now U.S. Pat. No. 4,429,698. Application Ser. No. 205,749 was itself a continuation of prior copending application Ser. No. 074,926, filed Sept. 13, 1979, now abandoned.

This invention relates to a device for applying a high frequency electromagnetic field to living tissue to promote healing thereof.

It has been known for many years that improved healing rates can be achieved by applying r.f. electromagnetic fields to wounded tissue. The therapeutic effects were considered to be due to heating of the tissue by the field and prior therapy apparatus has been configured to produce r.f. energy levels for tissue heating either on the surface or deep into the tissue. This heating technique is known as diathermy. It is known to pulse the r.f. field produced by diathermy apparatus. A specific example of the healing effects achieved with a pulsed field diathermy apparatus is given in "A Trial Involving the Use of Pulsed Electromagnetic Therapy on Children Undergoing Orchidopexy" R. H. C. Bentall and H. B. Eckstein, Zeitschrift fur Kinderchirurgie und Grenzgebiete p. 380–398 November 1975.

Heretofore the pulsed electromagetic field has been produced by hospital or laboratory based equipment comprising an electrical signal generator which feeds an induction coil mounted on a stand positioned adjacent an area of a patient to be treated. This apparatus is bulky and has the disadvantage that a patient cannot be treated on a continuous intensive basis without being hospitalised.

More recently, it has been appreciated that the therapy produced by an applied r.f. field is not characterised solely in terms of the tissue heating effect of the field. A discussion of this subject is given in my paper entitled "Healing by Electromagnetism-Fact or Fiction" New Scientist April 22, 1976.

I have devised lower powered portable apparatus for producing the electromagnetic field, suitable for being attached to a patient. Such protable apparatus is described in my British patent application published Feb. 27, 1980 under No. 2027594.

This portable apparatus comprises a battery driven r.f. oscillator and an antenna which is flexible to overlie an area of tissue to be treated. The apparatus thus can be attached to the patient and left running on a substantially continuous basis. The portable apparatus produces an electromagnetic field typically in the frequency range 3–30 MHz, the particular r.f. frequency not being of great significance as to the efficacy of the therapy. The r.f. field is pulsed in a manner to maximise the therapeutic effect. The field is of a strength which does not produce any significant tissue heating. The portable device thus operates at much lower power levels than the bulky diathermy apparatus, typically to produce r.f. field of less than 100 mw cm$^{-2}$ as measured at the skin of the tissue, and utilising a fundamentally different premise as to the manner in which a r.f. field may be utilised to effect treatment, namely that the field does not have to produce tissue heating in order to produce an improved healing rate.

A disadvantage of the portable device is that its antenna transmits electromagnetic energy not only in a forward direction towards the tissue, but also in a rearward direction outwardly from the patient with the result that a substantial portion of the transmitted energy does not pass into the tissue. Also, the outwardly passing energy may upset operation of laboratory or domestic electronic equipment. Furthermore, the prior flexible insulating substrate presents an undesirable water and air impervious barrier over a wound which may impede healing in certain circumstances.

SUMMARY OF THE INVENTION

According to the present invention from a first aspect there is provided a device for applying a high frequency electromagnetic field to tissue of the patient to promote healing, comprising an antenna for directing the field to the patient, and an electrical oscillator circuit arranged to energise the antenna to propagate electromagnetic energy for promoting healing of the tissue but without producing any significant heating thereof, the antenna having a directive pattern so configured that a substantially greater proportion of said energy is propagated in a forward direction for treating the tissue than in an opposite rearward direction so as to minimise emission of said energy outwardly of the patient.

To this end, the antenna may comprise a transmitting element arranged to be energised by the oscillator circuit to propagate said energy, and reflector means for reflecting into said forward direction energy transmitted from said transmitting element in said rearward direction. Preferably the reflector means is so arranged that the energy reflected thereby constructively adds to the energy propagated by the transmitting element in said forward direction.

The antenna may include additionally or alternatively to said reflector means, an absorber arranged to absorb said energy transmitted in the rearward direction.

The antenna may include a parasitic element for modifying the natural directive pattern of transmission of said energy from the transmitting element.

Preferably, the transmitting element comprises an electrical conductor arrangement formed as a loop encompassing a space permitting passage of fluids thereby allowing a wound in the tissue to breathe. If desired the space may include a wound dressing. The electrical conductor arrangement may comprise a loop of coaxial cable.

From a second aspect, the present invention provides an improvement relative to my prior portable device wherein the antenna is configured to transmit a spatially uniform electromagnetic field over at least a major portion of an area encompassed by the antenna when in use facing tissue to be treated.

In accordance with this second aspect of the invention it is possible to provide more predictable and quantifiable treatments than has been possible hitherto, because with the prior portable device the field strength to which the tissue is subjected varies across the spatial extent of the antenna and thus different tissue regions receive in effect different treatment conditions.

Preferably the uniform field antenna is configured as a flexible sheet like member to conform to a patients's body. For example, the antenna can comprise a flexible printed circuit which additionally carries components of a low voltage oscillator, typically powered by a battery.

In accordance with both aspects of the invention the inherent inductance of the antenna may be used as part of an L.C. circuit which defines the frequency of oscillation of the r.f. oscillator which energises the antenna, in a manner described in more detail in my British patent application published under No. 2027594.

BRIEF DESCRIPTION OF THE DRAWINGS

In order that the invention may be more fully understood embodiments thereof will now be described by way of illustrative example with reference to the accompanying drawings wherein.

DETAILED DESCRIPTION OF THE PREFERRED EMBODIMENTS

Figure 1:
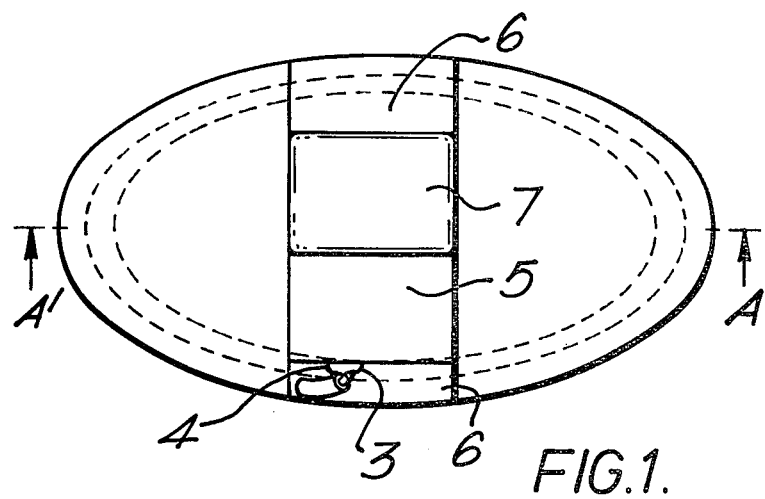
FIG. 1 is a schematic plan view of a device in accordance with the invention.
Figure 2:
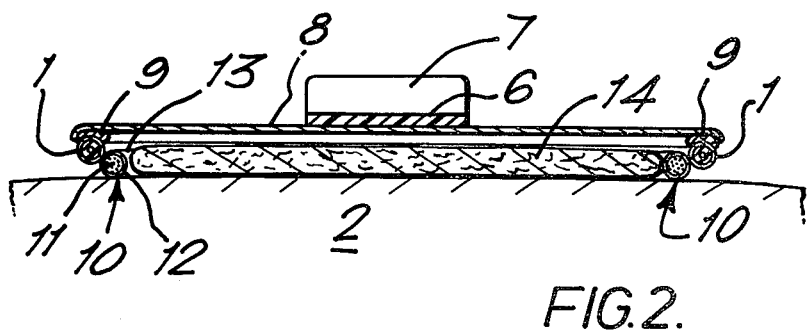
FIG. 2 is a sectional view of the device shown in FIG. 1 taken along line A'-A.

Referring firstly to FIGS. 1 and 2, the device includes a loop of coaxial cable 1 arranged in a suitable shape for overlying a wound, sore or like damaged area of tissue 2. The loop is flexible to conform to the surface of the patient's skin. At one end the cable 1 has its inner conductor 3 and its shielding sheath conductor 4 connected in an r.f. oscillator, the major part of which comprises a circuit 5 shown schematically, the circuit 5 being mounted on a plastics support substrate 6 which bridges the coaxial cable loop and is affixed thereto. The support substrate 6 also carries a battery power supply 7 for the oscillator. The circuit 5 cooperates with the cable 1 to produce in the cable r.f. pulses at a predetermined repetition rate. The r.f. frequency may be in the range 3 to 30 MHz and desirably 27.12 MHz as this is a legally allowed frequency for medical uses.

However the precise value of r.f. frequency does not appear to be critical with regard to the efficacy of the treatment. The loop of coaxial cable 1 acts as the transmitting element of an antenna and propagates the r.f. energy pulses. The natural transmission directive pattern in radial section of the coaxial cable 1 is substantially uniform, and thus the r.f. energy tends to be transmitted by the cable 1 both in a forward direction towards the tissue 2 to be treated and also in a rearward direction away from the patient.

However, in addition to the transmitting element 1, the antenna includes a reflector 8 which may comprise a flexible metal mesh or a sheet of metal foil, which reflects the rearwardly directed r.f. energy propagated by the cable 1. The reflector 8 is suitably spaced from the coaxial cable 1 by means of a dielectric spacer layer 9, such that the r.f. energy reflected by the reflector 8 constructively adds to the energy transmitted by the cable 1 in the forward direction, thereby improving the r.f. energy density received by the tissue 2.

The antenna may include a parasitic element 10 comprising a loop formed of a plurality of turns of copper conductor wire 11 contained within a sheath 12. The effect of the parasitic element 9 is to modify the natural directive pattern of r.f. propagation from the loop of cable 1, such as to reduce emission in directions transverse to the forward direction, and thus provide the antenna with a main lobe in the forward direction.

Additionally, the antenna may include r.f. absorbing material (not shown) for selectively absorbing rearward or sideways emitted r.f. radiation, so as to modify the directive pattern of the antenna as may be desirable in certain circumstances. Reflector 8 may be such an absorber, if grounded through the oscillator.

It is to be noted that the cable loop 1 surrounds an open space 13 which may overlie a wound and which permits the wound to breathe. The space may include a wound dressing (not shown).

The antenna is desirably driven to produce r.f. power density measured at the skin of the tissue 2 of less than 100 milliwatts $cm^{-2}$ and preferably of the order of microwatts $cm^{-2}$. This does not produce any significant heating of the tissue. The repetition rate of the r.f. pulses is selected such to maximise the efficacy of the treatment. Typically, the pulse repetition rate is in the range 0.1 Hz to 10,000 Hz.

At r.f. frequencies, the coaxial cable presents an inductance between its inner conductor 3 and its shielding inductor 4. This inductance is utilised as a frequency determining component of the oscillator circuit 5. This arrangement has the advantage that the circuit 5 need not include any inductors. The oscillator essentially comprises an L.C. circuit fed by a transistor, of which the L component is defined by the inductance of the coaxial cable wherein the oscillator components, apart from the L component are contained by the circuit 5. The circuit 5 can therefore be conveniently fabricated as a monolithic integrated circuit.

In a modification to the described device, the support substrate 6 which carries the circuit 5 and the battery power supply 7, may be detachable from the antenna, for re-use with a new antenna over a different wound.

The antenna may include on its front face a self adhesive material for attachment to the skin. The self adhesive material may extend outside of the perimeter defined by the cable loop 1.

It will be appreciated that the antenna described herein is flexible and can conform to the shape of the skin of a patient. While as shown in FIG. 1, the coaxial cable 1 is arranged in an elliptical loop, it may be arranged in other shapes selected to conform to contours of particular parts of the anatomy, for example the jaw or the nose, the limbs or the trunk. A pair of the antennas can be configured in a manner similar to a pair of goggles, for treatment of the eyes.

Also, more than one antenna can be driven by a common oscillator circuit. The oscillator circuit may be arranged to drive the antennae in a predetermined sequence.

In an alternative embodiment, the conductors of the transmitting element and the parasitic element may be formed in a loop on a flexible printed circuit board, and the reflector may be formed by a metallisation layer or pattern on the board. Preferably the antenna is configured to present to the tissue a substantially uniform spatial r.f. power density at least over a major portion of the area of the antenna facing the tissue.

Figure 3:
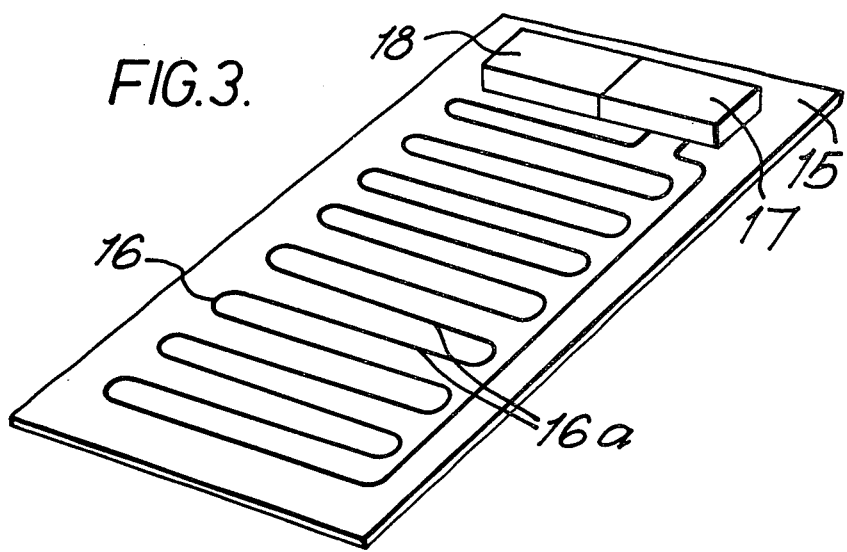
FIG. 3 is a schematic illustration of another device according to the invention, for producing a spatially uniform field.
Figure 4:
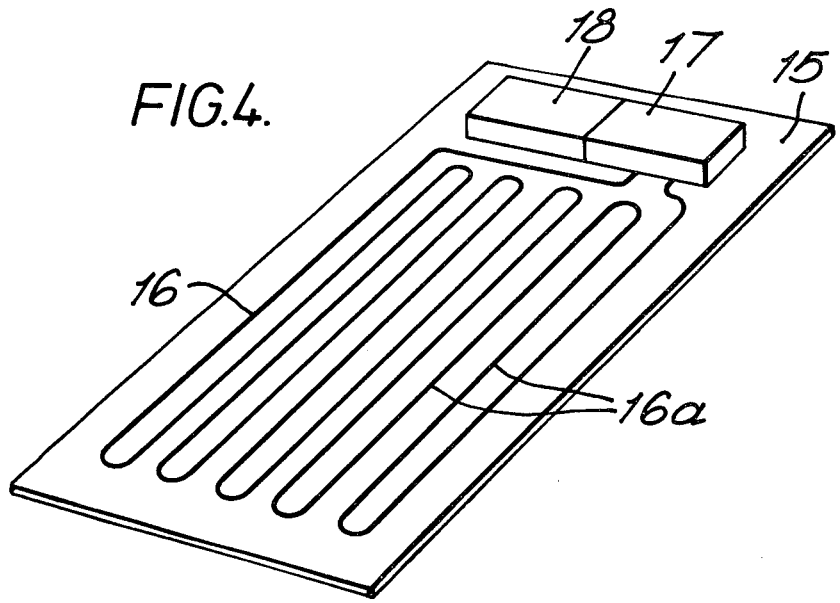
FIG. 4 is a schematic illustration of another device according to the invention for producing a uniform field.

The devices shown in FIGS. 3 and 4 are illustrative of embodiments which achieve a spatially uniform electromagnetic r.f. field for treating a patient, the field being uniform over at least a major portion of the spatial extent of the antenna which in use faces the patient. The teaching of the spatially uniform field given hereinafter with reference to FIGS. 3 or 4 may be used in combination with the teachings given in relation to FIGS. 1 and 2, or separately.

Referring to FIG. 3 a flexible printed circuit substrate 15 carries an antenna comprising a metallisation pattern 16 as shown, which is connected to an integrated circuit 17 mounted on the substrate. The integrated circuit 17 is powered by a battery supply 18 also mounted on the substrate. It will be appreciated that the circuit 16 and battery 17 may correspond to the circuit 5 and battery 7 of FIG. 2. In use, the substrate 15 overlies living tissue to be treated, and typically is attached to a patient's skin by adhesive means, not shown. The integrated circuit 17 comprises components of an oscillator and timer circuit arranged to energise the metallisation pattern 16 with r.f. pulses. As described with reference to FIG. 2, the inductance of the antenna may be used as a frequency determining component of the oscillator. The frequency of the r.f. energy typically lies within a range of 3–30 MHz, and is conveniently 27.12 MHz. It will be seen that the metallisation pattern 16 encompasses a given substrate area and will thus treat a corresponding area of the patient's tissue which underlies the substrate 15. The metallisation pattern 16 is so configured that there is emitted in the direction of the tissue a pulsed r.f. electromagnetic field which has a substantially uniform field strength at least over a major portion of the substrate 15. The field strength is desirably not greater than 100 mw cm$^{-2}$ and preferably is of the order of microwatts cm$^{-2}$. This field strength does not produce any significant tissue heating. The metallisation pattern includes a plurality of linear conductor portions 16a running parallel to one another transversely of the length of the substrate 15.

The r.f. pulse repetition rate is selected such as to maximise the efficacy of the treatment.

The flexible substrate 15 has the advantage of being able to conform to the surface of the skin of a patient, and thus can wrap around a limb for example.

The device shown in FIG. 4 is similar to that of FIG. 3 but with the conductor portions 16a running longitudinally of the substrate 15.

Many modifications and variations within the scope of the invention will be apparent to those skilled in the art. For example, rather than using a flexible printed circuit, the pattern of conductor portions defining the antenna can be formed from a serpentine conductor arranged in either of the patterns shown in FIGS. 3 or 4, with an electrically insulating covering holding the conductor in its serpentine configuration.

What is claimed is:

1. A device for applying a high frequency electromagnetic field to tissue of a patient to promote healing, comprising:
    an antenna for directing the field to the patient;
    an oscillator circuit arranged to energize the antenna to propagate electromagnetic energy for promoting healing of the tissue but without producing any significant heating thereof; and,
    means for constraining the electromagnetic energy propagated by the antenna to a directive pattern wherein a substantially greater proportion of said energy is propagated in forward direction for treating the tissue than in an opposite rearward direction so as to minimize emission of said energy outwardly of the patient.

2. A device for applying a radio frequency electromagnetic field to tissue of the patient to promote healing thereof, comprising;
    a flexible antenna for conforming to the shape of the patient;
    a battery;
    an electrical oscillator means for being driven by the battery and arranged to energize the antenna to propagate radio frequency electromagnetic energy for promoting healing of the tissue but without producing any significant heating thereof; and,
    means for constraining the electromagnetic energy propagated by the antenna to a directive pattern wherein a substantially greater proportion of said energy is propagated in a forward direction for treating the tissue than in an opposite rearward direction so as to minimize emission of said energy outwardly of the patient.

3. A device according to claims 1 and 2, wherein said antenna comprises a transmitting element arranged to be energised by the oscillator circuit to propagate said energy; and, reflector means for reflecting into said forward direction energy transmitted from said transmitting element in said rearward direction.

4. A device according to claim 3, wherein said reflector means is spaced from the transmitting element by a predetermined distance necessary for the energy reflected by the reflector means to be in phase with, and additive to the energy transmitted by the transmitting element in said forward direction.

5. A device according to claims 1 or 2, further comprising a layer of radiation absorbing material for absorbing energy transmitted in said rearward direction.

6. A device according to claim 2, wherein said antenna includes a parasitic element for modifying the natural directive pattern of transmission of said energy from said transmitting element.

7. A device according to claim 3, wherein the transmitting element comprises an electrical conductor arrangement formed as a loop defining an open space therein, permitting passage of fluids to and from a wound in the tissue.

8. A device according to claim 7, further comprising a wound dressing disposed in said space.

9. A device according to claim 3, wherein said transmitting element comprises a loop of coaxial cable.

10. A device according to claim 3, wherein said antenna encompasses a given area for treating a corresponding area of tissue, and said antenna is arranged to produce said field with spatially uniform field strength over at least a major portion of said given area.

11. A device for applying a high frequency electromagnetic field to tissue of the patient to promote healing, comprising;
    an antenna for overlying tissue of the patient, said antenna encompassing a given area for treating a corresponding tissue area of the patient; and,
    an electrical oscillator means arranged to energize the antenna to propagate electromagnetic energy for promoting healing of the tissue without producing any significant tissue heating thereof, said antenna having a plurality of linear conducting portions arranged to produce said field with a spatially uniform field strength over at least a major portion of said given area.

12. A device for applying a radio frequency electromagnetic field to tissue of the patient to promote healing thereof, comprising;
    a flexible antenna for conforming to the shape of the patient, said antenna encompassing a given area for treating a corresponding (tissue area of the patient;

a battery; and, an electrical oscillator circuit arranged to energize the antenna to propagate electromagnetic energy for promoting healing of the tissue but without producing any significant tissue heating, said antenna having a plurality of linear conducting portions arranged to produce said field with a spatially uniform field strength over at least a major portion of said given area.

13. A device according to claim 12 wherein said antenna comprises a flexible insulating substrate for overlying a patient's tissue and, a metalized pattern formed on the substrate.

14. A device according to claims 2 or 11, wherein said antenna presents an inductance to the radio frequency energy produced by the oscillator means, and said inductance comprises a frequency determining circuit component of said oscillator means.

* * * * *